United States Patent [19]
Hoeppner et al.

[11] Patent Number: 6,165,222
[45] Date of Patent: Dec. 26, 2000

[54] METHOD AND APPARATUS FOR ENABLING ACCESS TO AN INTRAMEDULLARY CANAL OF A FEMUR THROUGH A FEMORAL KNEE JOINT PROSTHESIS

[75] Inventors: Jacy Charles Hoeppner, Columbia City; David Ray Brown; Gregory David VanDeWater, both of Warsaw; Joel C. Higgins, Claypool; Brian David Salyer, Warsaw, all of Ind.

[73] Assignee: Biomet, Inc., Warsaw, Ind.

[21] Appl. No.: 09/223,616

[22] Filed: Dec. 30, 1998

[51] Int. Cl.[7] .......................................................... A61F 2/38
[52] U.S. Cl. ...................................... 623/20.15; 623/20.36
[58] Field of Search .............................. 623/20.14, 20.15, 623/20.21, 20.36

[56] References Cited

U.S. PATENT DOCUMENTS

| | | |
|---|---|---|
| 5,147,406 | 9/1992 | Houston et al. . |
| 5,152,796 | 10/1992 | Slamin ....................................... 623/20 |
| 5,181,925 | 1/1993 | Houston et al. . |
| 5,326,359 | 7/1994 | Oudard . |
| 5,330,534 | 7/1994 | Herrington et al. . |
| 5,370,702 | 12/1994 | Jones . |
| 5,387,242 | 2/1995 | Miser . |
| 5,405,349 | 4/1995 | Burkinshaw et al. . |
| 5,405,395 | 4/1995 | Coates . |
| 5,405,398 | 4/1995 | Buford, III et al. . |
| 5,554,158 | 9/1996 | Vinciguerra et al. . |
| 5,556,433 | 9/1996 | Gabriel ....................................... 623/20 |
| 5,593,449 | 1/1997 | Roberson, Jr. . |
| 5,681,353 | 10/1997 | Li et al. . |
| 5,683,472 | 11/1997 | O'Neil ....................................... 623/20 |
| 5,782,929 | 7/1998 | Sederholm . |
| 5,879,391 | 3/1999 | Slamin ....................................... 623/20 |

OTHER PUBLICATIONS

Biomet, Inc., *AGC Total Knee System, Tradition Series*, copyright 1995.
Biomet, Inc., *Performance The Total Knee System*, copyright 1997.
Biomet, Inc., *Maxim The Complete Knee System*, copyright 1995.
Biomet, Inc. Medical Products, *Biomet Retrograde Femoral Nail*, copyright 1995.
Biomet, Inc., *Biomet Retrograde Femoral Nail Surgical Technique*, copyright 1995.
Richards,*Genesis Total Knee System Bone Augmentation: Stems and Wedges*.
*The Journal of Bone and Joint Surgery*, Aug. 1997, 79–A.

*Primary Examiner*—Michael J. Milano
*Attorney, Agent, or Firm*—Harness, Dickey & Pierce, P.L.C.

[57] ABSTRACT

A method and apparatus for enabling access to an intramedullary canal of a femur through a femoral knee joint prosthesis includes a first condylar portion and a second condylar portion. The first condylar portion has a first femoral bearing surface and the second condylar portion has a second femoral bearing surface. An intercondylar portion extends between the first condylar portion and the second condylar portion and defines an opening passing therethrough. A seal member is operable to substantially seal the opening such that the seal member is further operable to be opened to enable access to the intramedullary canal of the femur without having to remove the femoral knee joint prosthesis from the femur. A method for enabling access to the intramedullary canal of the femur through the femoral knee joint prosthesis is also provided.

40 Claims, 7 Drawing Sheets

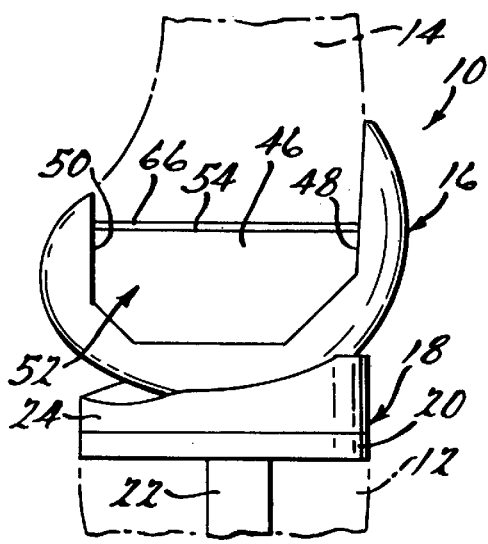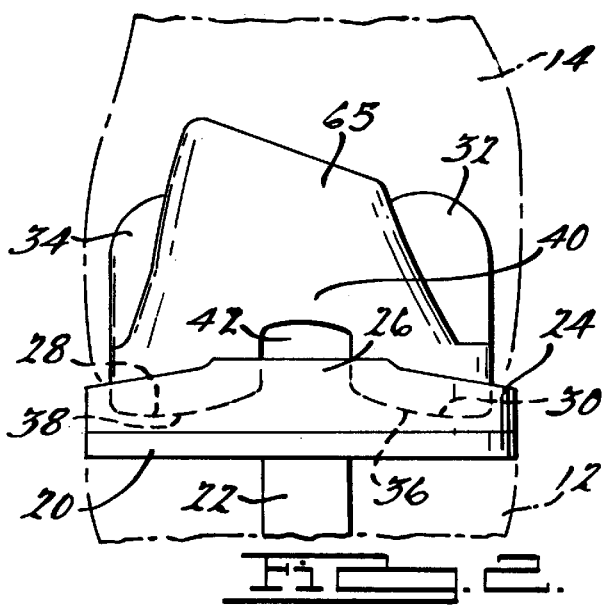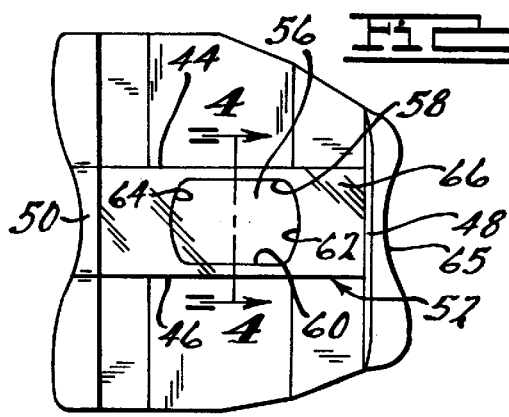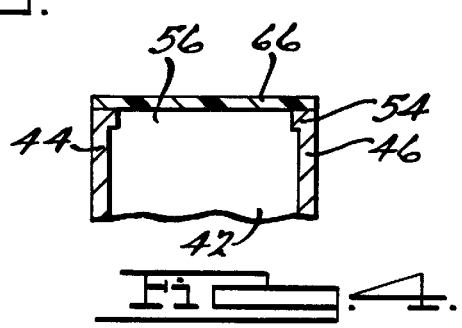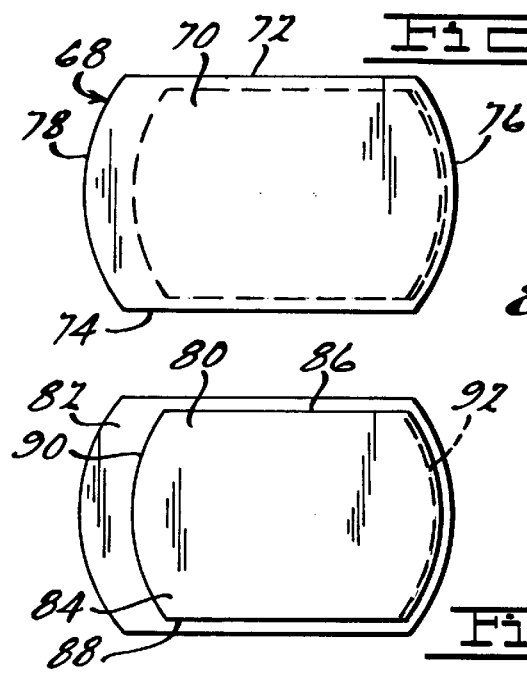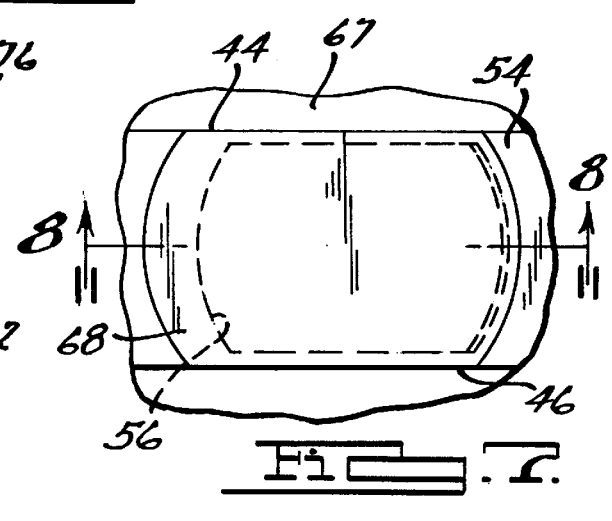

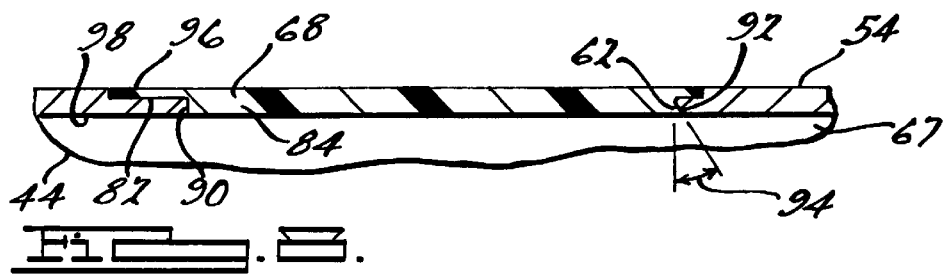
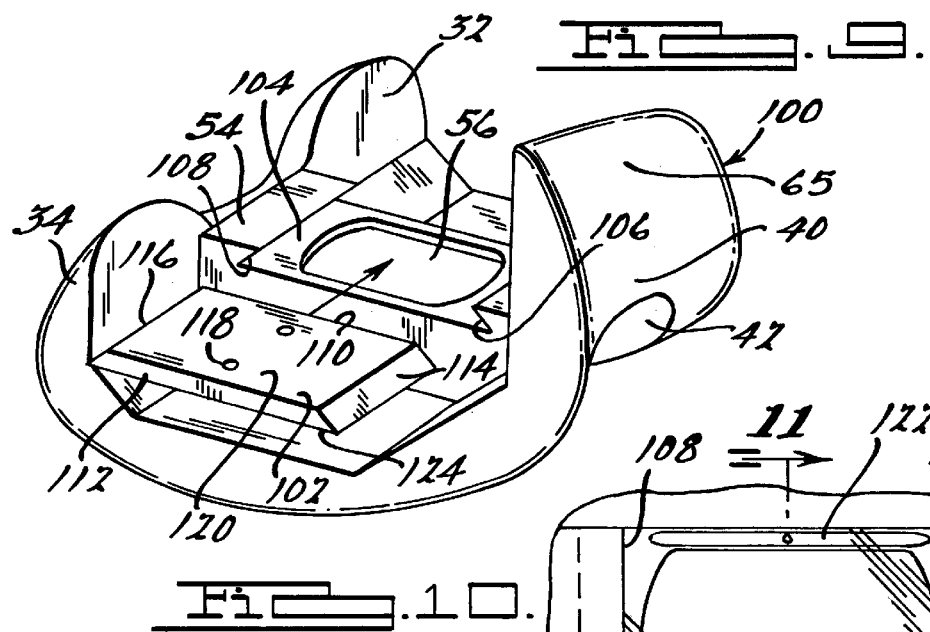
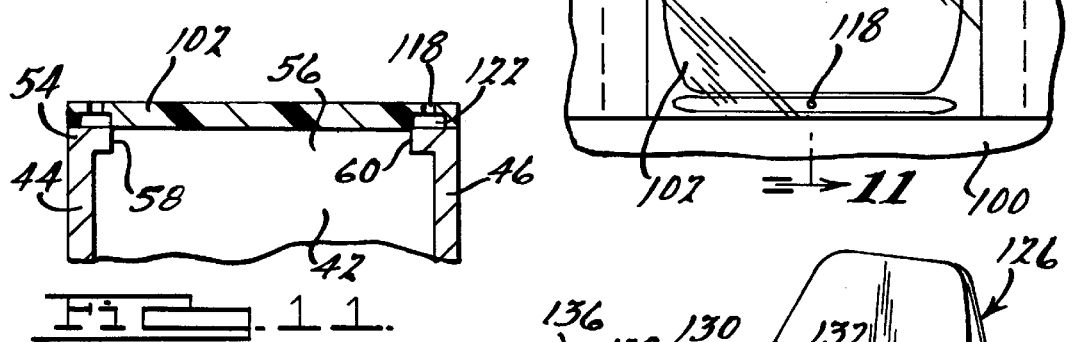
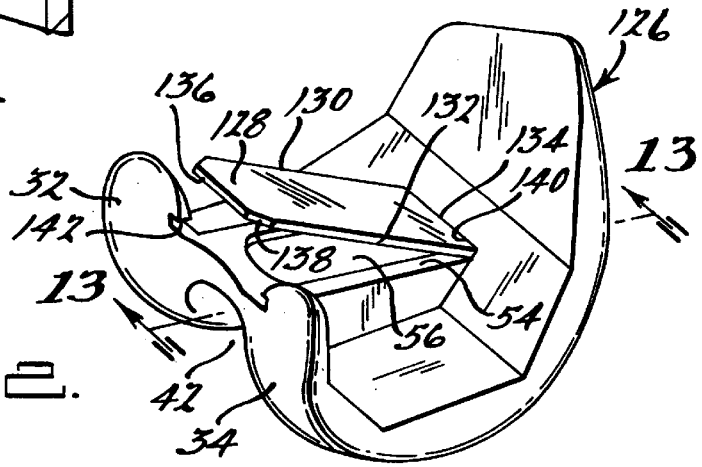

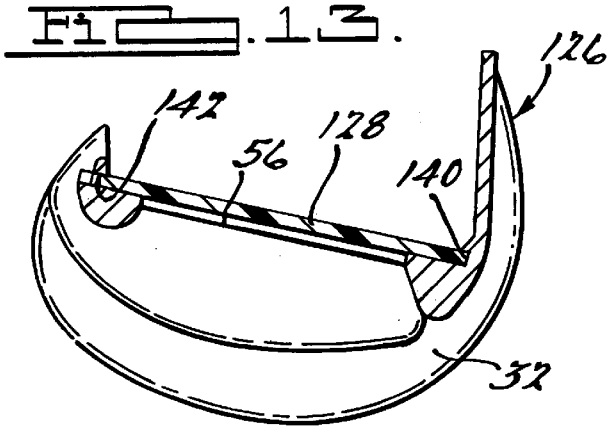
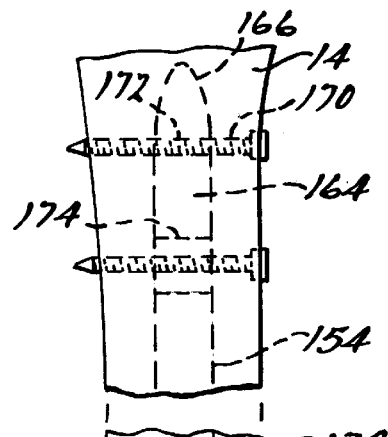
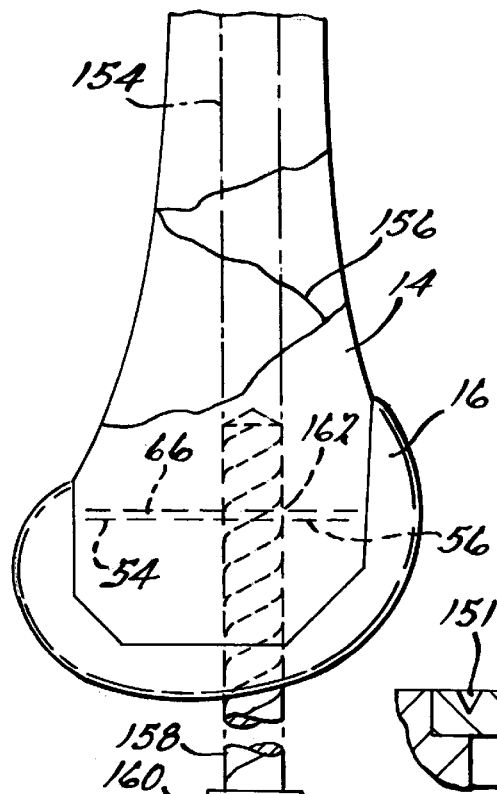
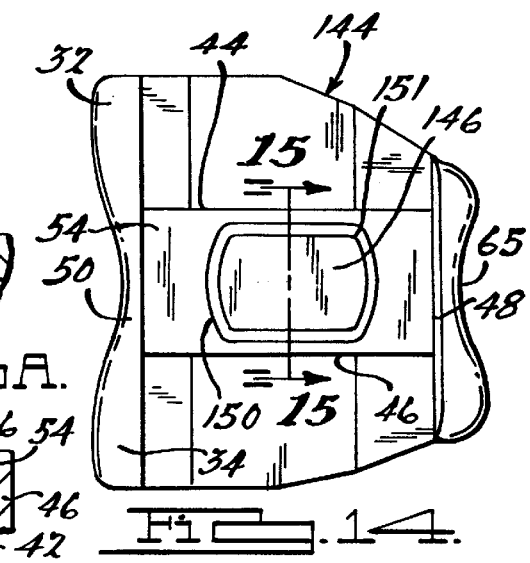
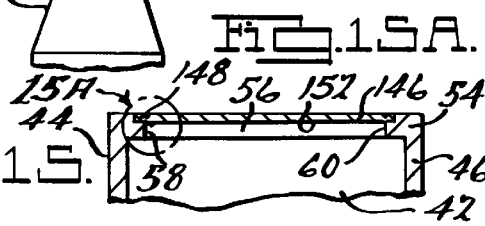

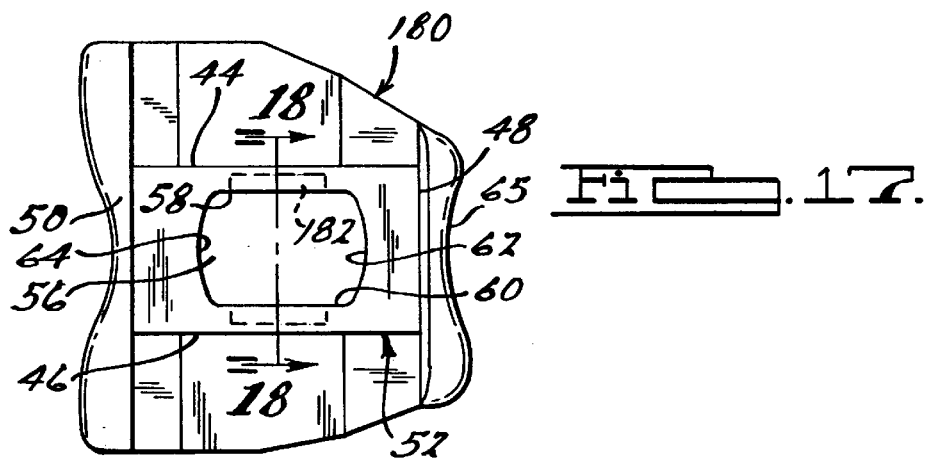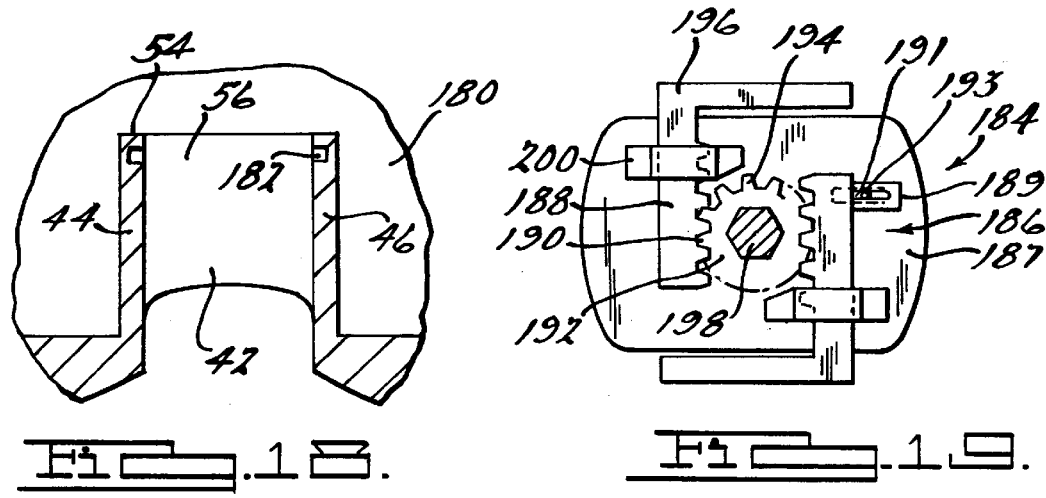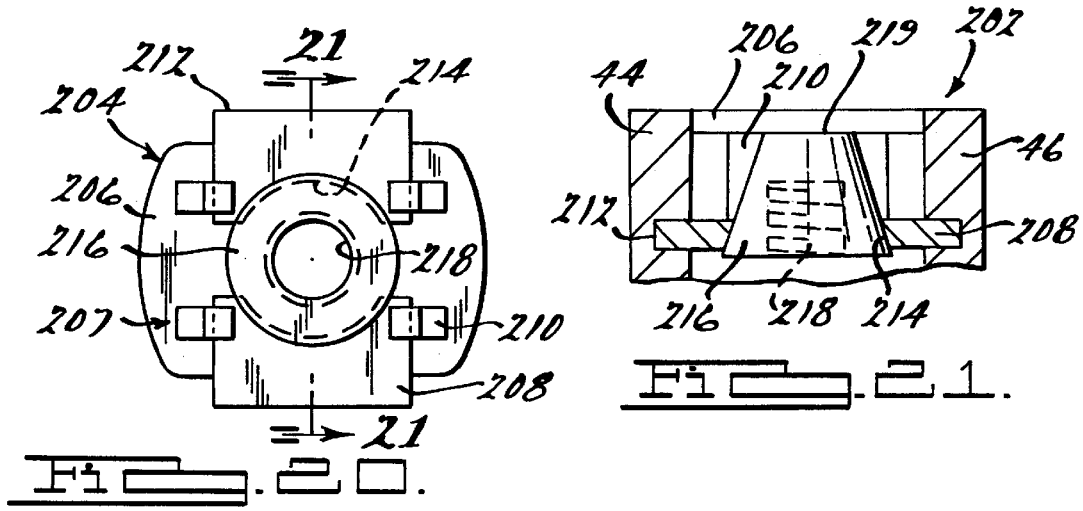

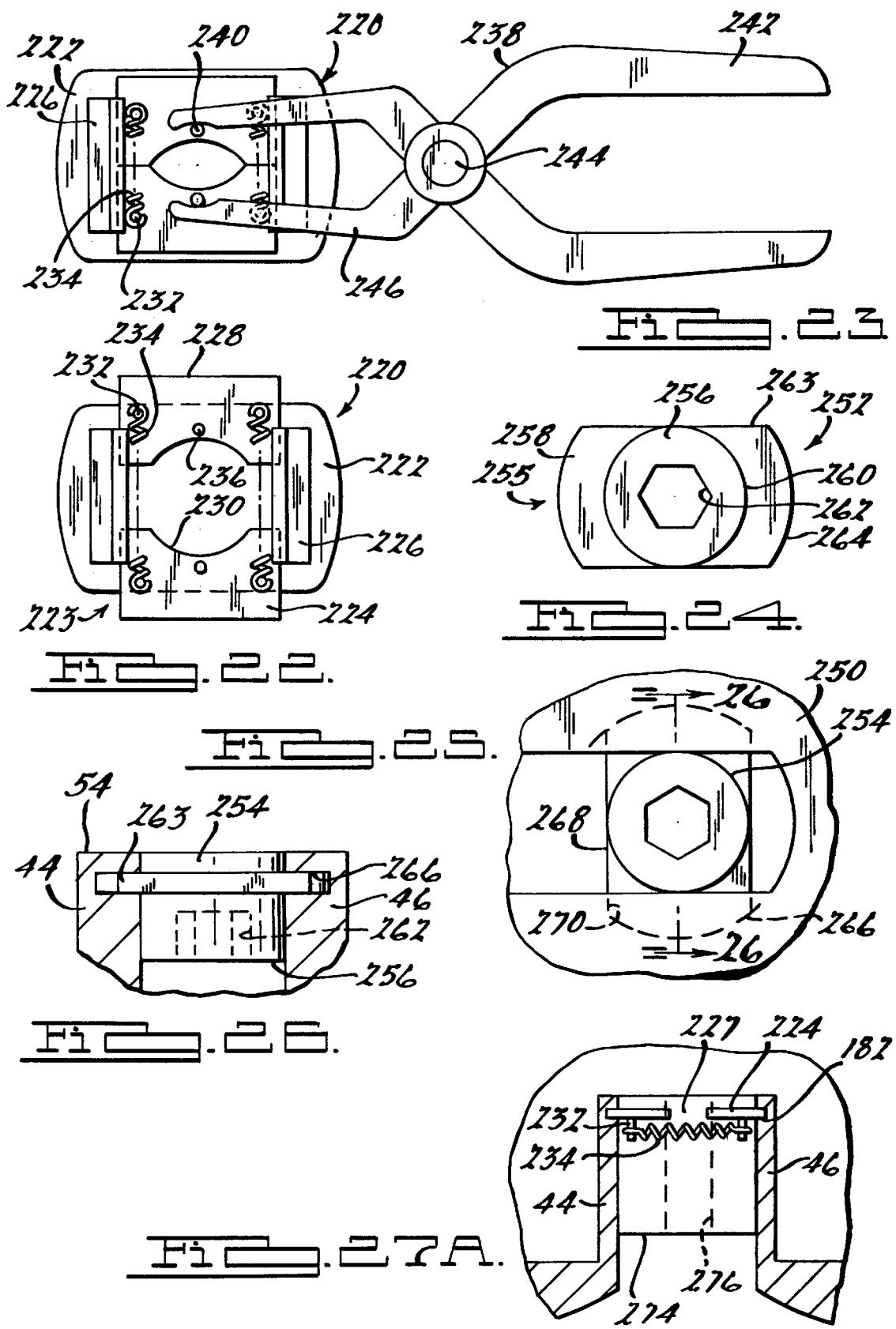

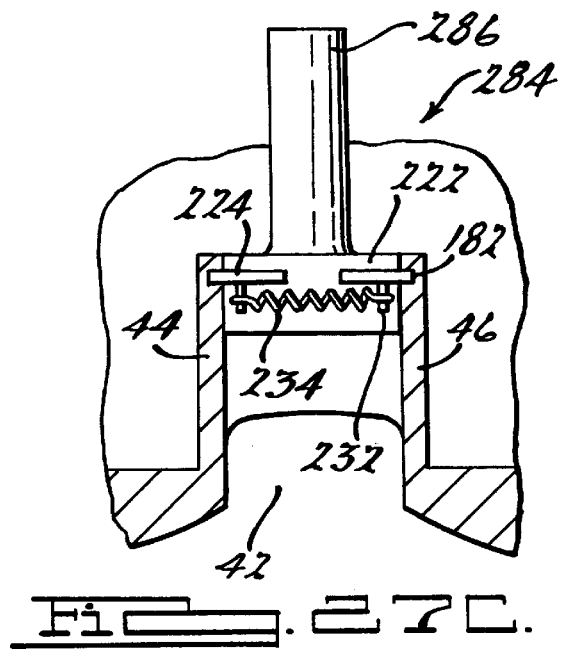
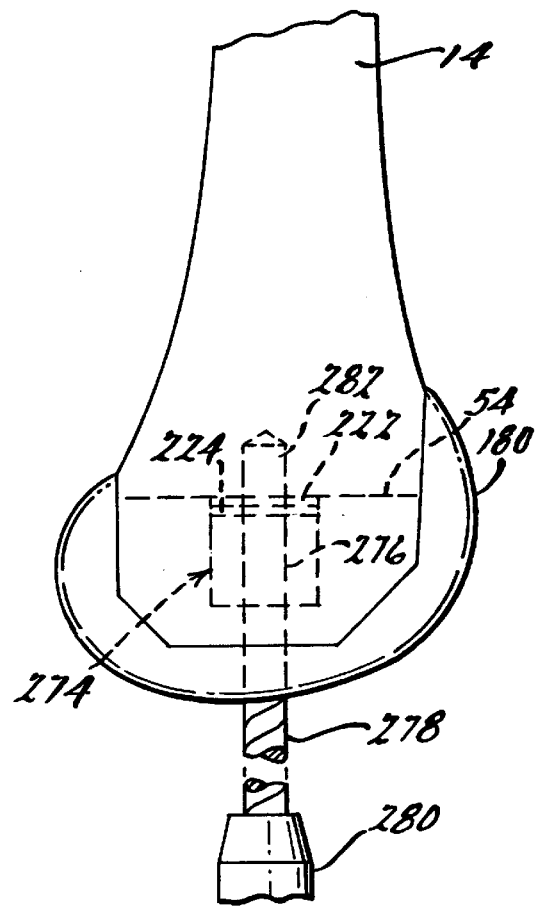
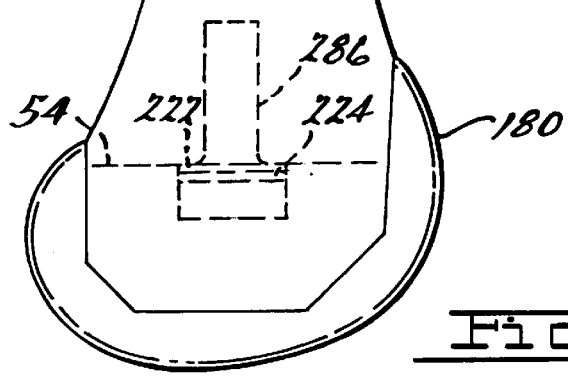

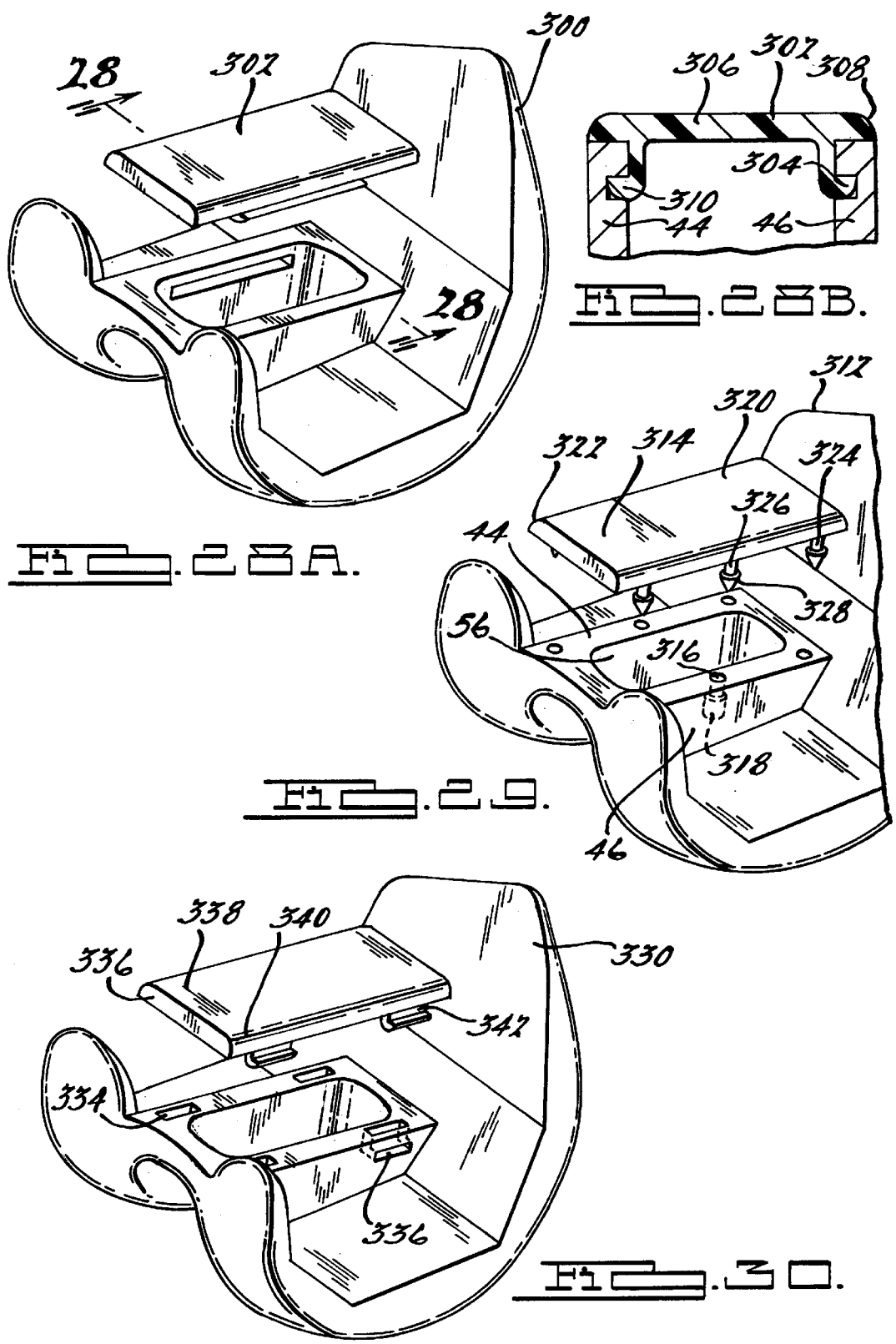

METHOD AND APPARATUS FOR ENABLING ACCESS TO AN INTRAMEDULLARY CANAL OF A FEMUR THROUGH A FEMORAL KNEE JOINT PROSTHESIS

BACKGROUND OF THE INVENTION

1. Field of the Invention

This invention relates generally to a method and apparatus for use in orthopedic surgical procedures, and more particularly, to a method and apparatus for enabling access to an intramedullary canal of a femur through a femoral knee joint prosthesis.

1. Discussion of the Related Art

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating the articulating motion of an anatomical knee joint.

Motion of a natural knee is kinematically complex. During a relatively broad range of flexion and extension, the particular surfaces of a natural knee experiences rotation, medial and lateral angulation, translation in the sagittal plane, rollback and sliding. Knee joint prostheses, in combination with the ligaments and muscles, attempt to allow natural knee motion, as well as absorb and control forces generated during the range of flexion. Depending on the degree of damage or deterioration of the knee tendons and ligaments, it may also be necessary for a knee joint prosthesis to limit one or more of these motions in order to provide adequate stability.

After the knee joint prosthesis is implanted into a patient, there may be situations which require access to the intramedullary canal of the femur, proximal to the femoral component. For example, should a supracondylar fracture occur above the anterior flange of the femur, this fracture may require a femoral nail to provide patient stability. Use of currently available posterior stabilized (PS) femoral components, however, pose various advantages and disadvantages when access to the intramedullary canal is required.

PS femoral components having a "closed box" provide the advantage of preventing debris migration into the articulating joint area, as well as preventing bone cement from passing through the opening to interfere with the tibial component. However, because the top of the box is closed, one way to insert a femoral nail involves removing the PS femoral component, implanting the femoral nail, and reimplanting a new revision PS femoral component. Alternatively, a high speed burr may be used to create a hole through the solid box, thereby creating sharp metal debris that may easily damage the rest of the femoral component.

Should an "open box" PS femoral component be utilized, a femoral nail may be passed through the top of the box and into the intramedullary canal without the disadvantages of the closed box. However, an "open box" PS femoral component also allows increased debris, bone chips or bone cement to pass through into the articulating joint area both during implantation and during use. As such, the use of "open box" or "closed box" PS femoral components each exhibit different advantages and disadvantages.

Another method for assisting in the healing of a supracondylar fracture or to improve patient instability is to modify the knee joint prosthesis with a constrained femoral component. This is generally achieved by providing a femoral component with an intramedullary stem that extends from the box. Here again, with existing stemmed femoral components, the stem is either integral with the femoral component or it must be attached to a modular femoral component before the component is implanted. In such cases, modular knee joint prosthetic devices are available which enables different boxes or different length stems to be coupled to the femoral component. However, these modular knee joint prosthetic devices require assembly before the prosthetic device is implanted and do not allow later intraoperative modification of the knee joint prosthesis without removal of the femoral component itself. This would, therefore, again require the femoral component to be removed with a new revision femoral component being subsequently implanted that has the intramedullary stem.

What is needed then is a method and apparatus for enabling access to an intramedullary canal of a femur through the femoral component of the knee joint prosthesis which does not suffer from the above mentioned disadvantages. This, in turn, will eliminate the need for removal of the femoral component to insert a femoral nail or a femoral stem; provide a closed box which has the advantage of preventing debris or bone cement from entering the articulating joint area; provide an easy mechanism to open the top of the box intraoperatively when it is desired to gain access to the intramedullary canal of the femur without having to remove the femoral component; reduce overall surgical cost, time and complexity to correct a supracondylar fracture; and provide a convertible sealed top which may be subsequently opened after the knee joint prosthesis has been implanted to provide the benefits of both a "closed box" femoral component and an "open box" femoral component. It is, therefore, an object of the present invention to provide such a method and apparatus for enabling access to an intramedullary canal of a femur through a femoral knee joint prosthesis.

SUMMARY OF THE INVENTION

In accordance with the teachings of the present invention, a method and apparatus for enabling access to an intramedullary canal of a femur through a femoral knee joint prosthesis is disclosed. This is basically achieved by providing a femoral knee joint prosthesis that defines a bore passing therethrough. A seal member seals the bore and is operable to be opened to enable access to the intramedullary canal of the femur.

In one preferred embodiment, a femoral knee joint prosthesis for allowing access to an intramedullary canal of a femur after the femoral knee joint prosthesis has been implanted includes a first condylar portion and a second condylar portion. The first condylar portion has a first femoral bearing surface and the second condylar portion has a second femoral bearing surface. An intercondylar portion extends between the first condylar portion and the second condylar portion and defines an opening passing therethrough. A seal member is operable to seal the opening in the top such that the seal member is further operable to be opened to enable access to the intramedullary canal of the femur without having to remove the femoral knee joint prosthesis from the femur.

In another preferred embodiment, a knee joint prosthesis for enabling access to an intramedullary canal of a femur includes a femoral component having at least one bearing surface and defining a bore passing therethrough. A tibial component having a second bearing surface is operable to articulate with the first bearing surface of the femoral component. A seal member is operable to seal the bore in the femoral component such that the seal member may be opened after the femoral component is implanted to enable access to the intramedullary canal of the femur.

In another preferred embodiment, a method for enabling access to an intramedullary canal of a femur through a femoral knee joint prosthesis includes implanting the femoral knee joint prosthesis having a seal member which seals a bore passing through the femoral knee joint prosthesis. Thereafter, the seal member in the femoral knee joint prosthesis is opened after the femoral knee joint prosthesis has been implanted to enable access to the intramedullary canal of the femur without removing the femoral knee joint prosthesis from the femur.

Use of the present invention provides a method and apparatus for enabling access to an intramedullary canal of a femur through a femoral knee joint prosthesis. As a result, the aforementioned disadvantages associated with the currently available "opened box" and "closed box" femoral knee joint prostheses have been substantially reduced or eliminated.

BRIEF DESCRIPTION OF THE DRAWINGS

Still other advantages of the present invention will become apparent to those skilled in the art after reading the following specification and by reference to the drawings in which:

FIG. 1 is a sagittal elevational view of a right knee joint having a knee joint prosthesis according to the teachings of a first preferred embodiment of the present invention;

FIG. 2 is a coronal elevational view of the knee joint prosthesis shown in FIG. 1;

FIG. 3 is a top view of the femoral component and a seal member of the knee joint prosthesis shown in FIG. 1;

FIG. 4 is a sectional view of the femoral component and seal member shown in FIG. 3 taken along line 4—4 in FIG. 3;

FIG. 5 is a top view of a seal member according to the teachings of a second preferred embodiment of the present invention;

FIG. 6 is a bottom view of the seal member shown in FIG. 5;

FIG. 7 is a partial top view of a femoral component and the seal member according to the teachings of the second preferred embodiment of the present invention;

FIG. 8 is a sectional view of the assembled femoral component and seal member shown in FIG. 7, taken along line 8—8 in FIG. 7;

FIG. 9 is a perspective view of a femoral component and seal member according to the teachings of a third preferred embodiment of the present invention;

FIG. 10 is a partial top view of the femoral component and seal member shown in FIG. 9;

FIG. 11 is a sectional view of the femoral component and seal member taken along line 11—11 in FIG. 10;

FIG. 12 is a perspective view of a femoral component and seal member according to the teachings of a fourth preferred embodiment of the present invention;

FIG. 13 is a sectional view of the femoral component and seal member shown in FIG. 12 taken along line 13—13 in FIG. 12;

FIG. 14 is a top view of a femoral component and seal member according to the teachings of a fifth preferred embodiment of the present invention;

FIG. 15 is a sectional view of the femoral component and seal member shown in FIG. 14 taken along line 15—15 of FIG. 14;

FIG. 15A is an enlarged sectional view of the femoral component and seal member shown in FIG. 15 taken about line 15A of FIG. 15;

FIGS. 16A–16B illustrate a method of implanting a femoral nail using the femoral component and seal member according to the teachings of the first preferred embodiment of the present invention;

FIG. 17 is a top view of a femoral component according to the teachings of a sixth preferred embodiment of the present invention;

FIG. 18 is a sectional view of the femoral component of FIG. 17 taken along line 18—18 of FIG. 17;

FIG. 19 is a bottom view of a seal member according to the teachings of the sixth preferred embodiment of the present invention;

FIG. 20 is a bottom view of a seal member according to the teachings of a seventh preferred embodiment of the present invention;

FIG. 21 is a sectional view of the femoral component and seal member of FIG. 20 taken along line 21—21 of FIG. 20;

FIG. 22 is a bottom view of a seal member according to the teachings of an eighth preferred embodiment of the present invention;

FIG. 23 is a bottom view of the seal member of FIG. 22 shown engaged with a retracting instrument;

FIG. 24 is a bottom view of a seal member according to the teachings of a ninth preferred embodiment of the present invention;

FIG. 25 is a partial bottom view of the femoral component and seal member according to the teachings of the ninth preferred embodiment of the present invention;

FIG. 26 is a sectional view of the femoral component and the seal member of FIG. 25 taken along line 26—26 of FIG. 25;

FIGS. 27A–27D illustrate a method for converting a non-stemmed femoral component according to the teachings of the eighth preferred embodiment of the present invention to a stemmed femoral component;

FIG. 28A is a perspective view of a femoral component and seal member according to the teachings of a tenth preferred embodiment of the present invention;

FIG. 28B is a sectional view of a femoral component and seal member taken along line 28—28 in FIG. 28A;

FIG. 29 is a perspective view of a femoral component and seal member according to the teachings of an eleventh preferred embodiment of the present invention; and FIG. 30 is a perspective view of a femoral component and seal member according to the teachings of a twelfth preferred embodiment of the present invention.

DETAILED DESCRIPTION OF THE PREFERRED EMBODIMENTS

The following description of the preferred embodiments concerning a method and apparatus for gaining access to an intramedullary canal of a femur through a femoral knee joint prosthesis are merely exemplary in nature and are not intended to limit the invention or its application or uses. Moreover, while the present invention is described in detail below with reference to specific types of knee joint prostheses, it will be appreciated by those skilled in the art that the present invention is clearly not limited to only the specific type knee joint prostheses mentioned herein and may be applied to various other knee joint prostheses.

Referring now to FIGS. 1 and 2, there is shown a knee joint prosthesis 10 in accordance with a first preferred embodiment of the present invention. The knee joint prosthesis 10 is functionally depicted as being secured to a tibia 12 and a femur 14 of a surgically resected right knee joint, with the tibia 12 and femur 14 being shown in phantom. It will be understood that while the knee joint prosthesis 10 is suited for implantation into a right knee joint, a suitable left knee joint prosthesis can be similarly constructed. Moreover, it will also be understood that each of the embodiments disclosed herein have the same overall configuration as shown in FIGS. 1 and 2.

The knee joint prosthesis 10 is generally known as a posterior stabilized (PS) knee joint prosthesis 10 which is designed to provide adequate stability in case of moderate deterioration and instability of the human knee. This most typically occurs when the anterior and posterior cruciate ligaments are sacrificed or dysfunctional and the medial and lateral collateral ligaments remain functionally intact. The knee joint prosthesis 10 includes a femoral component 16 and a tibial component 18. The knee joint prosthesis 10 may be based upon any closed box or opened box knee joint prosthesis, such as that disclosed in U.S. Pat. No. 5,330,534, which is hereby incorporated by reference. The knee joint prosthesis 10 may also be based upon the "Performance® Total Knee System", "Ascent™ Total Knee System", "AGC® Tradition Total Knee System" or the "Maxim Complete Knee System" each available from Biomet, Inc. of Warsaw, Ind. In other words, it is to be understood that the knee joint prosthesis 10 may be based upon various knee joint prosthetic platforms and be designed to include the various features of the preferred embodiments of the present invention.

Generally, the tibial component 18 is adapted to be secured to the proximal end of the tibia 12 after the tibia has been resected in a manner well known in the art. The tibial component 18 includes a platform like tibial tray 20 and an inferiorly extending tibial stem 22. The tibial stem 22 is adapted to be received in a corresponding opening made by the surgeon in the longitudinal center of the tibia 12. The tibial stem 22 may include a bore passing therethrough which is able to receive a suitable support member which is secured to the tibia 12 in a manner well known in the art. Should additional fixation be required, holes can be provided in the tibial tray 20 through which bone screws may be passed to secure the tibia tray 20 to the end of the tibia 12. The tibial tray 20 and stem 22 is preferably manufactured from Ti-6Al-4V or any other suitable biocompatible material.

Positioned atop the tibial tray 20 is a tibial insert 24. The tibial insert 24 is preferably formed from a surgical grade, low friction, low wearing plastic, such as UHMWPE or other suitable materials. The tibial insert 24 includes a stabilizing post 26 and first and second articulating or bearing regions 28 and 30 which articulate with the femoral component 16. The tibial insert 24 is secured to the tibial tray 20 by any suitable means. It should be noted that the only limitation the tibial component 18 places on the femoral component 16 is that the stabilizing post 26 be cleared by the femoral component 16.

The sealable convertible femoral component 16 generally includes a first condylar portion 32 and a second condylar portion 34 which have a first femoral bearing surface 36 and a second femoral bearing surface 38, respectively. The first and second condylar portions 32 and 34 of the femoral component 16 are interconnected by an intercondylar portion 40 which defines an intercondylar recess 42. The intercondylar portion 40 defining the intercondylar recess 42 includes a first lateral sidewall 44 and a second lateral sidewall 46 which are planar and substantially parallel to each other. The anterior portions of the first and second lateral sidewalls 44 and 46 are connected by an anterior wall 48 and the posterior portions of the first and second lateral sidewalls 44 and 46 are connected by a posterior wall 50. The intercondylar portion 40 which includes the first and second lateral sidewalls 44 and 46 and the anterior and posterior walls 48 and 50 define the perimeter of a box 52 that defines the intercondylar recess 42.

Positioned atop the box 52 is a substantially planar integral top 54 which defines an opening or bore 56. The opening 56 is defined by opposed planar parallel sidewalls 58 and 60 and arcuate anterior and posterior endwalls 62 and 64, respectively. The femoral component 16 including the box 52 is preferably formed as a unitary structure and preferably cast of a biocompatible high strength alloy such as a cobalt-chromium-molybdenam alloy or other suitable material. All surfaces which do not contact the femur 14 are preferably highly polished. The femoral component 16 further includes an arcuate patellar portion 65 which is disposed on the anterior surface of the femoral component 16. The patellar portion 65 is shaped to allow anatomical tracking of a natural or prosthetic patella. The patella prostheses which are compatible with the present invention may be of varying shapes such as round, oval or dome shaped and may be constructed from polyethylene, polyethylene with metal backing, or other suitable materials.

In order to substantially seal, close or cover the opening 56 in the top 54 of the box 52 such that the box 52 may be subsequently opened or breached after implantation of the femoral component 16, a convertible seal member 66 is provided. The seal member 66 is substantially rectangular in shape and formed from polymethylmethacrylate (PMMA) which is a transparent material or any other suitable material having any other suitable shape. The seal member 66 is secured to the top 54 of the box 52 by use of an adhesive or other appropriate securing mechanism further discussed herein. The seal member 66 is preferably 1–2 mm thick and provides a substantially fluid tight seal atop the box 52. However, it should be noted that the seal member 66 does not have to provide a fluid tight seal and merely needs to close or cover most of the opening 56. In other words, the seal member 66 may be made out of a screen or mesh material or not necessarily be sealed around the entire periphery of the opening 56. Since the seal member 66 is formed from PMMA, the seal member may be opened or breached subsequent to implantation of the femoral component 16 should access to the intramedullary canal of the femur 14 be required.

The seal member 66 may be opened or breached by any appropriate means such as drilling, puncturing or by simply driving a femoral nail directly through the seal member 66 in the case of repairing a supracondylar fracture. The seal member 66 closes or seals the box 52 and provides the surgeon with a substantially transparent window through opening 56 which can be used to assist in the implantation of the femoral component 16. The closed box 52, via the seal member 66 further provides and prevents bone cement or other debris from entering the articulating joint area between the femoral component 16 and the tibial component 18. Should it be subsequently required to obtain access to the intramedullary canal of the femur 14, the femoral component 16 does not require removal and the convertible seal member 66 may simply be breached by any appropriate means. Any debris caused from this breach will not pose a problem since the seal member 66 is made from PMMA, which is bone cement material and consistent with normal preparation.

Turning to FIGS. 5–8, a second preferred embodiment of a sealable convertible femoral component 67 is shown which utilizes a seal member 68. In this regard, like reference numerals will be used to identify like structures. The seal member 68 includes a top planar surface 70 defined by first and second planar and substantially parallel sidewalls 72 and 74 and anterior and posterior arcuate sidewalls 76 and 78. The sidewalls 72 and 74 meet or extend out substantially to lateral sidewalls 44 and 46, while arcuate sidewalls 76 and 78 extend out beyond arcuate sidewalls 62 and 64. Positioned about the underside 80 of the seal member 68 is a stepped shoulder 82 which extends substantially about the periphery of the seal member 68. The stepped shoulder 82 defines a region 84 which substantially mates within the opening or bore 56. The region 84 includes sidewalls 86 and 88 and a posterior arcuate sidewall or endwall 90 which are substantially perpendicular to the planar underside 80 that forms a recessed geometry. An anterior arcuate sidewall or endwall 92 angles inward at an angle of about 60 degrees, identified by reference numeral 94. This angled sidewall 92 mates with the corresponding anterior endwall 62 which is machined or cast to have a mating angular surface for this embodiment.

The seal member 68 is mated with the femoral component 67 by first inserting the anterior sidewall 92 of the seal member 68 adjacent the anterior sidewall 62 of bore 56. Once aligned, the posterior portion of the seal member 68 is tilted downward into position such that the stepped shoulder 82 mates with a stepped cutout region 96 formed about the bore 56 in the femoral component 67. This provides mechanical securement or a mechanical connection mechanism between the seal member 68 and to the femoral component 67, shown in FIG. 8. To provide a fluid tight seal, an adhesive may be applied between the stepped shoulder 82 on the seal member 68 and the cutout region 96 machined into the top 54 of the box 52. The top 70 of the seal member 68 is shown substantially flush with the top 54 of the box 52 and the underside or bottom 80 is substantially flush with the underside 98 of the box 52. However, the top 70 of the seal member 68 may also be raised (up to 50–70 mm) to accommodate for a constrained post on the tibial component 18.

Here again, the seal member 68 is formed from PMMA and, thus, provides a transparent window through the top of the box 52 or other suitable material. As with the seal member 66, the seal member 68 may be opened or breached by drilling, piercing, etc. after the femoral component 67 has been implanted onto the femur 14 should it be required to gain access to the intramedullary canal of the femur 14. Alternatively, the seal member 68 may be formed from a temperature dependent material or from two types of material, one of which is temperature dependent. In other words, the seal member 68 may be formed such that when the seal member 68 is warmed to a temperature similar to body temperature, the seal member 68 expands to be secured within the top of the box 52 such that when the material is cooled, it retracts or contracts to be removed from the top of the box 52. Still further, the seal member 68 may be formed from a material that reacts with certain chemicals such that the adhesive or a portion of the seal member 68 may be removed or dissolved upon reacting with another component applied to the seal member 68. This will also enable the seal member 68 to be easily removed. Finally, the seal member 68 may be formed from a high density polyethylene and thermo-mechanically bonded over the opening 56 in the box 52.

Referring now to FIGS. 9–11, a third preferred embodiment of a sealable convertible femoral component 100 is shown with a seal member 102. Here again, like reference numerals will be used to describe like structures. In this regard, the box 52 of the femoral component 100 includes the top 54 defining the bore 56. The top 54 defines a cutout region 104 having opposed anterior and posterior angled sidewalls or endwalls 106 and 108 which angle downward at about 45 degrees (45°) relative to the top 54 or at any other appropriate angle that is less than 90° or greater than 0°. The depth of the cutout region 104 is substantially equal to the thickness of the seal member 102. The seal member 102 is again formed from PMMA and includes first and second planar parallel sidewalls 110 and 112 and angled anterior and posterior sidewalls or endwalls 114 and 116, respectively. The seal member 102 further includes a pair of bores 118 passing through a top 120 of the seal member 102 which are in communication with elongated oval chambers or pockets 122.

The underside 124 of the seal member 102 slidably mates with the cutout region 104, as the anterior and posterior sidewalls 114 and 116 mechanically communicate with angled anterior and posterior sidewalls 106 and 108. This provides a mechanical connection mechanism to create mechanical securement which prevents the seal member 102 from being pushed outward substantially perpendicular to the top 54 when a force is applied to the underside 124 to breach or open the seal member 102. To provide further mechanical securement of the seal member 102 atop the box 52, an appropriate adhesive can be injected through bores 118, thereby flowing into elongated oval pockets 122. Additionally, adhesive may be thinly applied to the top of the cutout region 104 and the angled sidewalls 106 and 108 before slidably receiving the seal member 102. Alternatively, pins, screws or other attachment mechanisms may also be used.

The third embodiment of the femoral component 100 having the seal member 102 operates in substantially the same manner as the first and second preferred embodiments. In this regard, the seal member 102 may be opened or breached by any suitable means, such as drilling, puncturing, etc. to enable access to the intramedullary canal of the femur 14. Access to the intramedullary canal would generally be required should there by a supracondylar fracture of the femur 14, thereby requiring a femoral nail to stabilize the femur 14.

FIGS. 12–13 illustrate a fourth preferred embodiment of a sealable convertible femoral component 126 having a seal member 128. In this regard, like reference numerals will be used to identify like structures with respect to the previous preferred embodiments of the present invention. Here again, the seal member 128 is formed from a PMMA or other suitable biocompatible material and includes laterally spaced planar parallel sidewalls 130 and 132 which mate with sidewalls 44 and 46. The seal member 128 further includes a planar anterior sidewall 134 and a planar posterior sidewall 136 having notched corners or angled sidewalls 138.

In this embodiment, the top 54 of the box 52 is substantially planar and defines the bore 56. The box 52 includes the lateral sidewalls 44 and 46 and the anterior intercondylar portion 40 defines an anterior slot 140 which is operable to nestingly receive the anterior sidewall 134 of the seal member 128. The posterior intercondylar portion 40 also defines a pair of notches 142 which extend adjacent the first and second condylar portions 32 and 34. The notch regions 142 are operable to nestingly and snappingly receive the angled sidewalls 138 adjacent the posterior sidewall 136 of the seal member 128 or the notch regions 142 can also slidably receive the seal member 128 from the posterior side.

The seal member 128 is installed by first engaging the anterior sidewall 134 of the seal member 128 with the anterior slot 140 of the femoral component 126. An adhesive may first be applied to the top 54 of the box 52 should this be desired. Once the anterior sidewall 134 is engaged within the anterior slot 140, the posterior angled sidewalls 138 are tilted into engagement with the femoral component 126 until the angled sidewalls 138 are snapped in place beneath the posterior notches 142 to provide mechanical securement. Since the seal member 128 is made from PMMA, the seal member 128 is able to be slightly flexed, enabling the seal member 128 to be snapped in place and secured within anterior and posterior grooves or slots 140 and 142, respectively. Here again, the seal member 128 may be used similar to the seal members set forth in the first, second and third embodiments. In this regard, the seal member 128 may be readily breached or opened should access be required to the intramedullary canal of the femur 14 after the femoral component 126 has already been implanted.

FIGS. 14 and 15 illustrate a fifth preferred embodiment of a sealable convertible femoral component 144 employing a seal member 146. In this regard like reference numerals will be used to identify like structures with respect to the previous preferred embodiments of the present invention. The top 54 of the box 52 defining the bore 56 includes a stepped counterbore 148 extending substantially about the periphery of the bore 56. The seal member 146 is sized to substantially mate with the counterbore region 148 when the seal member 146 is nestingly received within the top 54. The seal member 146 is preferably formed from a thin metallic foil such as cobalt-chromium-alloy, having a thickness of about 0.01 mm–0.025 mm. The seal member 146 is secured to the femoral component 144 atop the box 52 by means of a weld 150 which extends substantially about the periphery of the bore 56. Alternatively, the seal member 146 may be cast directly into the femoral component 144. In other words, the seal member 146 would simply be a thinned region (0.01 mm–0.25 mm) formed directly from a casted femoral component 144 and having substantially the same structure and function as described above.

Since the seal member 146 is formed from a thin metallic foil or area, the seal member 146 will have a higher impact resistance as compared to seal members made from PMMA. The seal member 146 may be opened or breached simply by puncturing the underside 152 of the seal member 146 either with an appropriate tool or by simply driving the end of a retrograde nail up through the seal member 146 after the femoral component 144 has already been implanted. The seal member 146 may also have a V-shaped depression 151 formed within the seal member 146 about its periphery that allows it to be easily peeled open or away. The V-shaped depression 151 can be engaged by a tool fashioned to engage the depression 151 to peel the seal member 146 out of the bore 56.

Turning to FIGS. 16A and 16B, a method for enabling access to an intramedullary canal 154 of the femur 14 will now be described in detail with respect to the first preferred embodiment of the femoral component 16. However, it will be understood by those skilled in the art that this method, or any other method of opening or breaching the particular seal member used may be employed with any of the embodiments discussed herein. First, after the femoral component 16 has been implanted onto the femur 14 using techniques well known in the art, there may be a necessity to gain access to the intramedullary canal 154 of the femur 14 should a supracondylar fracture 156 occur with the patient. In such a case, the femoral component 16 does not require removal from the femur 14 and the convertible sealed box 52 may simply be opened, exposed or breached by any appropriate means. In this example, a drill bit 158 driven by a driver 160 is employed to bore an access hole through the PMMA seal member 66. Since the seal member 66 is formed from PMMA, debris does not pose a problem. Once an opening 162 is created in the seal member 66 through the box 52 and the intramedullary canal 154 by drilling or reaming, the drill 158 is removed from the box 52, and a femoral nail 164 is driven through the opening 162 in the box 52 upward into the intramedullary canal 154 of the femur 14.

The femoral nail may be any conventional femoral nail, such as that provided by Biomet of Warsaw, Indiana and referred to as a "Biomet Retrograde Femoral Nail". The femoral nail 164 includes a rounded end 166 and a blunt end 168. Passing laterally through the femoral nail 164 is a pair of distally positioned threaded anchor screws 170 that extend through a bore 172 and an elongated bore 174. A pair of proximally positioned threaded anchor screws 175 pass through bores 176 and are substantially rotated 90 degrees (90°) relative to screws 170. As shown in FIG. 16B, the femoral nail 164 longitudinally extends through the intramedullary canal 154 substantially through and along the supracondylar fracture 156 and into dense cortical bone region 178 to provide overall stability of the fractured femur 14. With the femoral nail 164 in place, the tibial component 18 is subsequently mated with the femoral component 16 in a conventional articulating manner. The surgery is completed without having to remove the femoral component 16. Such a procedure substantially reduces surgical time, cost and complexity, as well as reduces the patient's recovery time.

Turning to FIGS. 17–19, a mechanically sealable convertible femoral component 180 according to the teachings of a sixth preferred embodiment of the present invention is shown. In this regard, like reference numerals will be used to identify like structure with respect to the other preferred embodiments of the present invention. The femoral component 180 includes the box 52 having top 54 which defines bore 56. The sidewalls 58 and 60 of the bore 56 extend to the inner lateral sidewalls 44 and 46 which define channels 182, shown clearly in FIG. 18. The lateral sidewalls 44 and 46 are also slightly thicker than in the first preferred embodiment.

A seal member 184 having a mechanical securing mechanism 186 is shown in FIG. 19 and is sized to be matingly received within bore 56. In this regard, the seal member 184 includes a substantially planar seal plate 187 having a pair of geared racks 188 that include teeth 190 that mate with a pinion gear 192 having teeth 194. The rack members 188 include a pair of latch members 196 which extend substantially perpendicular to the rack members 188. Upon rotating the pinion 192, via a hex drive 198, the teeth 194 of the pinion 192 engage the teeth 190 of the rack 188, thereby enabling the latches 196 to be extended or retracted relative to the seal member 184 as they slide beneath retaining members 200. To maintain the rack member 188 in an extended position, a catch 189 formed from a spring biased pin 191 holds one rack member 188 in an extended position, which also holds the other rack member 188 in an extending position. Thus, the latch 189 must also be disengaged, via the hole 193 in the pin 191, to move the rack members 188. All of the components of the seal member 184 are made from a biocompatible material such as cobalt-chromium-alloy.

The seal member 184 is installed by rotating the pinion 192 counterclockwise, via the hex drive 198, using an appropriate hex head wrench to retract the latch members 196 within the outer periphery of the seal plate 187. Once retracted, the seal member 184 is slidably received between the lateral sidewalls 44 and 46 until the latch members 196 are aligned with channels 182. Once aligned, the pinion 192 is again rotated clockwise with an appropriate hex head wrench, thereby extending the latch members 196 within channels 182 to securely retain the seal member 184 atop and within the box 52.

Should access to the intramedullary canal be required to repair a supracondylar fracture, the seal member 184 is simply removed, via rotating the pinion 192 counterclockwise, thereby disengaging the latches 196 from within the channels 182 and simply removing the seal member 184 from between the lateral sidewalls 44 and 46. Alternatively, should the patient be exhibiting instability after the PS femoral component 180 is implanted and it is desired to provide a fully constrained femoral component 180, additional stabilization of the femoral component 180 is required, via an axially extending intramedullary stem which is coupled to the femoral component 180. In this case, such a stem can be mounted on the top of the seal member 184 and installed by simply removing the seal member 184 without the stem and engaging a new seal member with the stem, as further discussed herein.

Referring to FIGS. 20–21, a sealable convertible femoral component 202 according to the teachings of a seventh preferred embodiment of the present invention is shown. In this regard, like reference numerals will be used to identify like structures. The femoral component 202 is substantially similar to the femoral component 180 except that the channels 182 are positioned further downward from the top 54 of the box 52. A seal member 204 is shown having a mating seal plate 206 which is snuggly received within the bore 56 and a mechanical securing mechanism 207. Positioned on the underside of the seal plate 206 are a pair of slidable latches 208 which are slidably secured under stepped brackets 210 which are welded to the underside of the seal plate 206. Each latch member 2.08 has a planar engagement sidewall 212 and an arcuate engagement sidewall 214 that has a slightly angled sidewall which angles at about 40 or less (self-locking). Each arcuate angled sidewall 214 slidably engage a conical plug 216 which forms a Morse-type taper and acts as a wedge mechanism. Alternatively, the conical plug 216 and the latches 208 may be threaded and threadably engage one another.

In other words, to install the seal member 204 within the femoral component 202, the wedge or plug 216 is removed from the seal member 202 by threadably engaging a threaded bore 218 with an appropriate removal tool and slidably retracting the latch members 208. Once retracted, the seal member 204 is slidably positioned between the sidewalls 44 and 46 to align the latch members 208 with the channels 182. Once aligned, the channel members 208 are slid apart from one another such that the engaging sidewalls 212 are nestingly received within the channels 182. Once engaged, the plug or wedge 216 is positioned between and against the angled arcuate sidewalls 214. The plug 216 is then impacted or threaded with an appropriate instrument until a bottom surface 219 of the plug 216 comes to rest atop the seal plate 206, thereby securing the seal member 204 within the femoral component 202. Should it be desired to gain access to the intramedullary canal of the femur 14, a removal tool is simply threadably received within threaded bore 218 of plug 216 and impacted away from the seal plate 206 to remove the plug 216. Once removed, the latch members 208 are retracted from the channels 182 and the seal member 204 is removed from the femoral component 202.

In FIGS. 22 and 23, an eighth preferred embodiment of a seal member 220 is shown which may be used with the femoral component 180 of FIG. 17. In this regard, the seal member 220 includes a seal plate 222 and a mechanical sealing member 223 having a pair of opposed latch members 224. The latch members 224 are slidably retained by stepped slide members 226 that are welded to the underside of seal plate 222. Each latch member 224 includes a planar engagement sidewall 228 and an inner arcuate sidewall 230. The planar sidewall 228 is operable to engage the channel 182, and the inner arcuate sidewall 230 enables access through the center of the seal plate 222, further discussed herein. Each latch member 224 further includes a pair of engagement pins 232 which retain a pair of resilient springs 234. The springs 234 are used to outwardly bias the latch members 224, as shown in FIG. 22.

In order to retract the latch members 224, a pair of opposed bores 236 are provided which may be engaged by a removal tool 238. To retract the latch members 224, a pair of posts 240 extending from the removal tool 238 are simply inserted within the bores 236 while the handle 242 is drawn together about pivot 244. With the latch members 224 fully retracted, the seal member 220 may be installed within the femoral component 180. Once the latch members 224 are aligned with the channel 182, the handle 242 is slowly released to allow the spring biased latches 224 to be nestingly received within the channels 182. It should further be noted that the arms 246 of the tool 238 are stepped to provide clearance for the tool 238 to extend within the interior of the box 52 that defines the intercondylar recess 42.

Referring to FIGS. 24–26, a ninth preferred embodiment of a sealable convertible femoral component 250 having a seal member 252 is shown. Here again, like reference numerals will be used to identify like structures. The femoral component 250 is substantially similar to the other femoral components, except that the elongated bore 56 is replaced with a circular bore 254 which passes through the top 54 of the box 52 and the sidewalls 44 and 46 are thicker in construction. The seal member 252 includes a mechanical securing mechanism 255 having a stepped cylindrical region 256 that extends from a seal plate 258 and is aligned with the bore 254. The cylindrical step portion 256 includes a cylindrical sidewall 260 and a hexagonal shaped bore 262 which is operable to be engaged with an appropriate hex head tool. The seal plate 258 includes a pair of opposed arcuate shaped wings 263 having arcuate sidewalls 264.

A semicircular channel 266 is formed within sidewalls 44 and 46, as well as anterior sidewall 48, as shown in FIG. 25. This semi-circular channel or slot 266 enables the seal member 252 to be substantially rotated, while wing members 263 nestingly and slidably engage the semi-circular channel 266. To install the seal member 252 within the femoral component 250, the seal member 252 is aligned between the sidewalls 44 and 46. With the wing members 263 aligned substantially along the semi-circular channel 266, the seal member 252 is rotated clockwise about 90 degrees (90°) until sidewall 268 engages edge 270 formed within sidewall 266, via a hex head drive engaging the bore 262. To remove the seal member 252, the seal member 252 is simply rotated counterclockwise until the wing members 263 are aligned between the sidewalls 44 and 46.

The seal members 184, 204, 220 and 252 shown in FIGS. 17–26 mechanically seal the top 54 of the box 52 in each of the particular femoral components. Each of the seal members 184, 204, 220 and 252 may be employed should a supracondylar fracture occur and a femoral nail be required to be inserted within the intramedullary canal of the femur 14. In this way, the particular seal member is simply mechanically removed as previously discussed and a femoral nail is simply passed through the bore 56 in the opened box 52. These embodiments may also be used to upgrade the particular femoral component from a posterior stabilized (PS) femoral component to a stemmed femoral component. In other words, with a stemmed femoral component, further support of the femoral component is required and thus, the femoral component requires a stem that extends up into the intramedullary canal. A method for gaining access to the intramedullary canal and modifying the posterior stabilized (PS) femoral component to a stemmed femoral component is shown in FIGS. 27A–27D.

FIGS. 27A–27D illustrate a method for converting the posterior stabilized (PS) femoral component 180 that employs the seal member 220 to a stemmed femoral component 180. It will also be understood by those skilled in the art that any of the embodiments shown in FIGS. 17–26 may be modified to include a drill guide and stem component as discussed herein. In this regard, the femoral component 180 having the sealed box 52 is first opened upon engaging the posts 240 of the retraction tool 238 within bores 236 of the seal member 220. Once engaged, the handle 242 is drawn together, thereby retracting the latch members 224 and enabling the removal of the seal member 220 from within the top of the box 52 and out from between the lateral sidewalls 44 and 46.

Once removed, a drill guide 274 may be installed within the femoral component 180, via engaging the pair of channels 182, using an identical mechanical engagement mechanism 223 as used with the seal member 220. The drill guide 274 includes a guide member 276 defining a guide bore 277 which may be used to guide a drill bit 278 driven by a driver 280 into the femur 14 (see FIG. 27B). A cavity 282 is then formed, via the drill 278, which is operable to slidably receive a stem, further discussed herein. Once the cavity 282 is formed, the drill 278 is removed and the drill guide 274 is disengaged from the femoral component 182, via the tool 238, in a substantially similar fashion as the seal member 220 is removed.

Once the drill guide 274 is removed, a stemmed component 284 having a stem 286 is implanted into the femur 14 similar to the way the seal 220 closes the bore 56. In this regard, the stem component 284 includes the same engagement mechanism 223 in the seal member 220 and may simply be installed utilizing the tool 238. Alternatively, the seal member 220 may be modular in that the stem 286 may be removably coupled to the seal member 220 after the seal member 220 is removed from the femoral component 180. Once installed, the posterior stabilized (PS) femoral component 180 is modified to a stemmed femoral component 180. This procedure substantially eliminates the need to remove the existing femoral component 180 and replace it with a new femoral component by enabling the top 54 of the box 52 to be opened from the exposed side of the femoral component 180 and replaced with a stem component. This reduces overall surgical cost, complexity and time, as well as recucing the patient's recovery time.

Turning now to FIGS. 28A–28B, a tenth preferred embodiment of a sealable convertible femoral component 300 having a seal member 302 is shown. Here again, like reference numerals will be used to identify like structures. The femoral component 300 is substantially similar to the other femoral components, except that elongated channels or grooves 304 are formed into the lateral sidewalls 44 and 46, shown clearly in FIG. 28B. The seal member 302 is again preferably formed by PMMA or other appropriate material such as UHMWPE. The seal member 302 includes a top 306 having rounded corners 308 and a pair of engagement members or elongated fingers 310 that snappingly engage grooves 304. The seal member 302 may be opened or breached by any appropriate means after the femoral component 300 has been implanted.

Referring to FIG. 29, an eleventh preferred embodiment of a femoral component 312 and seal member 314 is shown. In this regard, like reference numerals will be again used to identify like structures. The femoral component includes a plurality of bores 316 having enlarged counterbores 318 extending through the lateral sidewalls 44 and 46 adjacent the opening 56. The seal member 314 again includes a top surface 320 having rounded corners 322 along with a plurality of engagement members 324. Each engagement member 324 includes a substantially cylindrical sidewall 326 and a conical end 328 which are adapted to be snappingly received within bore 316 and counterbore 318, respectively. Again, the seal member 314 may be formed from PMMA, or any other appropriate material. Accordingly, the seal member 314 again may be opened by any appropriate means to gain access to the intramedullary canal of the femur 14 after the femoral component 312 has been implanted.

Finally, turning to FIG. 30, a femoral component 330 and a seal member 332 according to the teachings of a twelfth preferred embodiment of the present invention is shown. The femoral component 330 includes four substantially rectangular bores 334 formed into the lateral sidewalls 44 and 46, each having a side opening 336. The seal member 332 again includes a top 338 having rounded corners 340 and four rectangular engagement members or legs 342. Each leg 342 includes a finger 344 extending therefrom which is operable to be snappingly received within and extend from side openings 336 of channels 334. Again, the seal member 332 may be formed from PMMA, or any other appropriate material and is operable to be opened or breached by any appropriate means.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A femoral knee joint prosthesis that provides access to an intramedullary canal of a femur after the femoral knee joint prosthesis has been implanted, said femoral knee joint prosthesis comprising:

a first condylar portion having a first femoral bearing surface;

a second condylar portion having a second femoral bearing surface;

an intercondylar portion extending between said first condylar portion and said second condylar portion defining an opening passing therethrough; and a seal member operable to substantially seal said opening in said intercondylar portion, wherein said seal member is further operable to be opened after the femoral knee point has been implanted to allow access to the intramedullary canal of the femur without having to remove the femoral knee joint prosthesis from the femur.

2. The femoral knee joint prosthesis as defined in claim 1 wherein said seal member is formed from polymethyl-methacrylate (PMMA).

3. The femoral knee joint prosthesis as defined in claim 1 wherein said seal member is substantially transparent.

4. The femoral knee joint prosthesis as defined in claim 1 wherein said intercondylar portion includes a superior top and said seal member does not extend substantially beyond said top into the intramedullary canal.

5. The femoral knee joint prosthesis as defined in claim 1 wherein said seal member is integral with said intercondylar portion and formed from a thinned region in said intercondylar portion that seals said opening.

6. The femoral knee joint prosthesis as defined in claim 1 wherein said intercondylar portion includes first and second lateral sidewalls and anterior and posterior endwalls that define a box having a top that defines said opening.

7. The femoral knee joint prosthesis as defined in claim 1 further comprising a securing mechanism to secure said seal member to said femoral knee joint prosthesis.

8. The femoral knee joint prosthesis as defined in claim 7 wherein said securing mechanism is selected from a group consisting of adhesive, welding, thermo-bonding and mechanical securement.

9. The femoral knee joint prosthesis as defined in claim 8 wherein said mechanical securement is selected from a group consisting of mating sidewalls, rack and pinion mechanism, Morse-type taper mechanism, spring-biased latches and rotatable wing members.

10. The femoral knee joint prosthesis as defined in claim 7 wherein said securing mechanism includes a bore passing through said seal member and a pocket in communication with said bore which is operable to receive an adhesive.

11. The femoral knee joint prosthesis as defined in claim 7 wherein said securing mechanism includes at least one angled sidewall on said seal member that mates with at least one angled sidewall that defines a portion of said opening.

12. The femoral knee joint prosthesis as defined in claim 11 wherein said at least one angled sidewall of said seal member is an arcuate angled sidewall which substantially mates with an arcuate angled sidewall that defines said portion of said opening.

13. The femoral knee joint prosthesis as defined in claim 7 wherein said securing mechanism includes a pair of opposed angled sidewalls on said seal member that mates with a pair of opposed angled sidewalls formed in a top of said intercondylar portion.

14. The femoral knee joint prosthesis as defined in claim 7 wherein said securing mechanism includes an anterior slot and a pair of posterior notches defined in said femoral knee joint prosthesis which are operable to be mated with an anterior end and a pair of angled sidewalls of said seal member.

15. The femoral knee joint prosthesis as defined in claim 7 wherein said securing mechanism includes a pair of geared rack members having a pair of latches and a geared pinion which mates with said geared rack to enable said pair of latches to be retracted or extended.

16. The femoral knee joint prosthesis as defined in claim 7 wherein said securing mechanism includes a pair of slidable latch members having opposed arcuate angled sidewalls which substantially mate with a conical plug.

17. The femoral knee joint prosthesis as defined in claim 7 wherein said securing mechanism includes a pair of spring biased latches which are operable to be retracted or extended.

18. The femoral knee joint prosthesis as defined in claim 7 wherein said securing mechanism includes a pair of rotatable wings which rotatably engage a semi-circular groove defined by said intercondylar portion.

19. The femoral knee joint prosthesis as defined in claim 1 wherein said seal member may be opened by any one of the following actions selected from a group consisting of drilling, puncturing, piercing, removing and breaching.

20. The femoral knee joint prosthesis as defined in claim 1 further comprising a removable drill guide which may be removably secured to said femoral knee joint prosthesis after implantation of said femoral knee joint prosthesis.

21. The femoral knee joint prosthesis as defined in claim 1 further comprising a removable stem operable to be secured to said femoral knee joint prosthesis after implantation of said femoral knee joint prosthesis.

22. The femoral knee joint prosthesis as defined in claim 21 wherein said stem is a modular stem which may be removably coupled to said seal member.

23. The femoral knee joint prosthesis as defined in claim 1 wherein said femoral knee joint prosthesis may be converted from a stemless femoral knee joint prosthesis to a stemmed femoral knee joint prosthesis after said femoral knee joint prosthesis has been implanted.

24. The femoral knee joint prosthesis as defined in claim 1 wherein said seal member provides a substantially fluid tight seal.

25. A knee joint prosthesis for enabling access to an intramedullary canal of a femur, said knee joint prosthesis comprising:
a femoral component having at least one bearing surface and defining a bore passing therethrough;
a tibial component having a second bearing surface operable to articulate with said first bearing surface of said femoral component; and
a seal member operable to substantially seal said bore in said femoral component, wherein said seal member may be opened after said femoral component is implanted to enable access to the intramedullary canal of the femur without having to remove the femoral knee joint prosthesis from the femur.

26. The knee joint prosthesis as defined in claim 25 further comprising a securing mechanism to secure said seal member to said femoral component.

27. The knee joint prosthesis as defined in claim 26 wherein said securing mechanism is selected from a group consisting of adhesive, welding, thermo-bonding and mechanical securement.

28. The knee joint prosthesis as defined in claim 27 wherein said mechanical securement is selected from a group consisting of mating sidewalls, rack and pinion mechanism, Morse-type taper mechanism, spring biased latches and rotatable wing members.

29. The knee joint prosthesis as defined in claim 25 wherein said seal member is substantially transparent.

30. The knee joint prosthesis as defined in claim 25 wherein said seal member is formed from a material selected from a group consisting of polymethylmethacrylate (PMMA), polyethylene, biocompatible thermoplastic, and thin metal foil.

31. A femoral knee joint prosthesis that provides access to an intramedullary canal of a femur, said femoral knee joint prosthesis comprising:
a first condylar portion having a first femoral bearing surface;
a second condylar portion having a second femoral bearing surface;
an intercondylar portion extending between said first condylar portion and said second condylar portion defining an opening passing therethrough; and means for sealing said opening in said intercondylar portion, wherein said means for sealing is operable to be opened after the femoral knee joint has been implanted to enable access to the intramedullary canal of the femur without having to remove the femoral knee joint prosthesis from the femur.

32. The femoral knee joint prosthesis as defined in claim 31 further comprising means for securing said means for sealing to said femoral knee joint prosthesis.

33. The femoral knee joint prosthesis as defined in claim 32 wherein said means for securing includes a plurality of engagement members extending from said means for sealing which are operable to securingly engage the femoral knee joint prosthesis.

34. A method for enabling access to an intramedullary canal of a femur through a femoral knee joint prosthesis, said method comprising:

implanting the femoral knee joint prosthesis having a seal member which substantially seals a bore passing through the femoral knee joint prosthesis; and opening the seal member in the femoral knee joint prosthesis to expose the bore after the femoral knee joint prosthesis has been implanted to enable access to the intramedullary canal of the femur without removing the femoral knee joint prosthesis from the femur.

35. The method as defined in claim 34 further comprising opening the seal member in the femoral knee joint prosthesis by removing the seal member from the femoral knee joint prosthesis.

36. The method as defined in claim 34 wherein opening the seal member in the femoral knee joint prosthesis further comprises breaching said seal member.

37. The method as defined in claim 34 further comprising securing a removable drill guide to the femoral knee joint prosthesis after opening the seal member in the femoral knee joint prosthesis and drilling a hole in the femur using the removable drill guide.

38. The method as defined in claim 37 further comprising removing the drill guide and inserting a seal member having a stem operable to be inserted into the hole formed in the femur.

39. The method as defined in claim 34 further comprising inserting a femoral nail into the intramedullary canal of the femur after opening the seal member in the femoral knee joint prosthesis without removing the femoral knee joint prosthesis from the femur.

40. A femoral knee point prosthesis that provides access to an intramedullary canal of a femur after the femoral knee joint prosthesis has been implanted, said femoral knee joint prosthesis comprising:

a first condylar portion having a first femoral bearing surface;

a second condylar portion having a second femoral bearing surface;

an intercondylar portion extending between said first condylar portion and said second condylar portion defining an opening passing therethrough; and a seal member formed from a thin metal foil and operable to substantially seal said opening in said intercondylar portion, wherein said seal member is further operable to be opened to allow access to the intramedullary canal of the femur without having to remove the femoral knee joint prosthesis from the femur.

* * * * *